United States Patent [19]

Kohn et al.

[11] Patent Number: 5,707,865

[45] Date of Patent: Jan. 13, 1998

[54] RETROVIRAL VECTORS FOR EXPRESSION IN EMBRYONIC CELLS

[76] Inventors: Donald B. Kohn, 4256 Jubilo Dr., Tarzana, Calif. 91356; Pia M. Challita, 15000 Moorpark, Apt. 311, Sherman Oaks, Calif. 91403-2445

[21] Appl. No.: 361,112

[22] Filed: Dec. 21, 1994

[51] Int. Cl.[6] .................. C12N 5/10; C12N 5/16; C12N 15/86

[52] U.S. Cl. .............. 435/325; 435/320.1; 435/235.1; 435/172.3; 435/352; 435/354; 536/24.1; 536/23.1; 424/93.1; 424/93.2; 424/93.21; 514/44; 935/22; 935/32; 935/66; 935/70

[58] Field of Search ............ 435/172.3, 240.2, 435/320.1, 325, 352, 354; 514/44; 424/93.1, 93.2, 93.21; 536/24.1, 23.1; 935/22, 32, 66, 70

[56] References Cited

PUBLICATIONS

Gordon, EM et al. "Gene Therapy Using Retroviral Vectors", Current Opinion in Biotechnology 5: 611–616 (1994).
Brenner, MK et al. "Gene Transfer into Human Hemopoietic Progenitor Cells", British Medical Bulletin 51(1):167–191 (1995).
Ostertag, et al., *J. Virol.*, vol. 33, No. 2, pp. 573–582 (Feb. 1980).
Linney, et al., *Nature*, vol. 308, pp. 470–472 (Mar. 29, 1984).
Gorman, et al., *Cell*, vol. 42, pp. 519–526 (1985).
Stocking, et al., *Virology*, vol. 153, pp. 145–149 (1986).
Franz, et al., *Proc. Natl. Acad. Sci.*, vol. 83, pp. 3292–9296 (May 1986).
Hilberg, et al., *Proc. Nat. Acad. Sci.*, vol. 84, pp. 5232–5236 (Aug. 1987).
Weiher, et al., *J. Virol.*, vol. 61, No. 9, pp. 2742–2746 (Sep. 1987).
Loh, et al., *Mol. Cell. Biol.*, vol. 7, No. 10, pp. 3775–3784 (Oct. 1987).
Bowtell, *J. Virol.*, vol. 62, No. 7, pp. 2464–2473 (Jul. 1988).
Flanagan, et al., *Mol. Cell. Biol.*, vol. 9, No. 2, pp. 739–746 (Feb. 1989).
Feuer, et al., *J. Virol.*, vol. 63, No. 5, pp. 2317–2324 (May 1989).
Loh, et al., *Mol. Cell. Biol.*, vol. 10, No. 8, pp. 4045–4057 (Aug. 1990).
Szyf, et al., *Mol. Cell. Biol.*, vol. 10, No. 8, pp. 4396–4400 (Aug. 1990).
Grez, et al., *Proc. Natl. Acad. Sci.*, vol. 87, pp. 9020–9206 (Dec. 1990).
Prince, et al., *J. Virol.*, vol. 65, No. 4, pp. 1803–1809 (1991).
Akgun, et al., *J. Virol.*, vol. 65, No. 1, pp. 382–387 (Jan. 1991).
Hoeben, et al., *J. Virol.*, vol. 65, No. 2, pp. 904–909 (Feb. 1991).
Petersen, et al., *Mol. Cell. Biol.*, vol. 11, No. 5, pp. 1214–1221 (Mar. 1991).
Grez, et al., *J. Virol.*, vol. 65, No. 9, pp. 4691–4698 (Sep. 1991).
Flanagan, et al., *Mol. Cell. Biol.*, vol. 12, No. 1, pp. 38–44 (Jan. 1992).

*Primary Examiner*—Christopher S. F. Low
*Attorney, Agent, or Firm*—Elliot M. Olstein; Raymond J. Lillie

[57] ABSTRACT

Retroviral plasmid vectors which include an enhancer region obtained from a virus selected from the group consisting of Myeloproliferative Sarcoma Virus and polyoma virus, and a primer binding site obtained from murine retrovirus. The retroviral plasmid vector does not include a negative control region. The vector also may include a nucleic acid sequence which encodes demethylation of cytosine residues in the proviral LTR. Such plasmid vectors are especially useful in the generation of retroviral vector particles which may be expressed in embryonic cells, such as embryonic stem cells.

12 Claims, 12 Drawing Sheets

SEQUENCE OF THE MULTIPLE CLONING SITE IN THE pGI PLASMID

| 1/2 EcoRI | NotI | SnaBI | SalI | BamHI | XhoI | HindIII | ApaI |
|---|---|---|---|---|---|---|---|
| AATTC | GCGGCCGC | TACGTA | GTCGAC | GGATCC | CTCGAG | AAGCTT | GGGCCC |
| G | CGCCGGCG | ATGCAT | CAGCTG | CCTAGG | GAGCTC | TTCGAA | CCCGGG |

1/2ClaI

AT

TAGC

FIG. 2

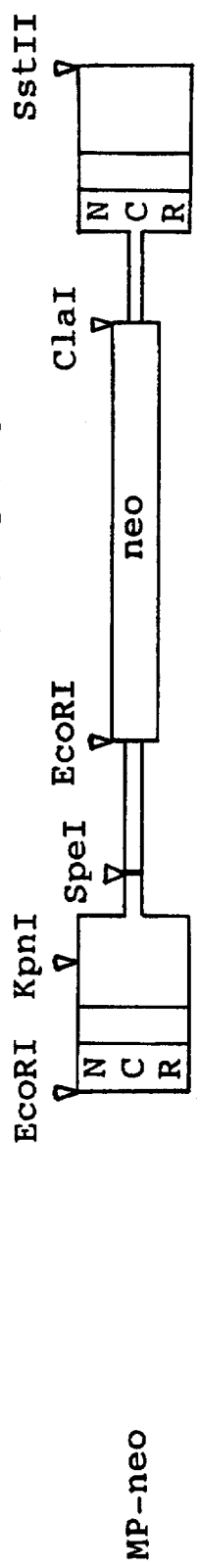
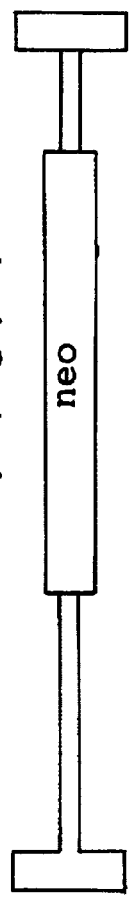
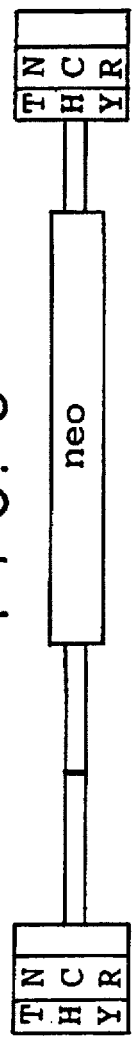
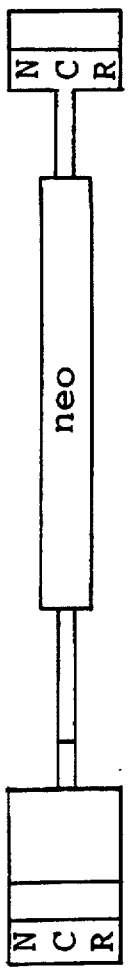

MP-ncr-dl-neo

MP-thy-dl-neo

L-ncr-neo

= d1587 rev pbs

☐ = MoMLV enhancer

= MPSV enhancer

T
H = Thy-1 fragment
Y

N = negative control
C region
R region 1 2 3 4 5 6 7 8 9 10 11 12 13 14 15 16

RETROVIRAL VECTORS FOR EXPRESSION IN EMBRYONIC CELLS

This invention relates to retroviral vectors. More particularly, this invention relates to retroviral vectors which provide for improved gene expression in embryonic cells and in embryonic stem cells.

BACKGROUND OF THE INVENTION

Moloney Murine Leukemia Virus based retroviral vectors have been introduced into large numbers of cells for the purpose of gene therapy; however, the Moloney Murine Leukemia Virus LTR has been observed to be inactive and become de novo methylated when transduced into embryonic carcinoma (EC) cell lines embryonic stem (ES) cells, and hematopoietic stem cells. (Linney, et al., Nature, Vol. 308, pgs. 470–472 (1984); Tsukiyama, et al., (Mol. Cell. Biol., Vol. 9 pgs. 4670–4676 (1989)). The inactivity of the enhancer is mediated by its interaction with negatively-acting cellular factors (Niwa, et al. Cell, Vol. 32, pgs. 1105–1113 (1983); Gorman, et al., Cell, Vol. 42, pgs. 519–526 91985); Weiher, et al., J. Virol., Vol. 61, pgs. 2742–2746 91987); Akgun, et al., J. Virol., Vol. 65, pgs. 382–388 (1991); Tsukiyama, et al., Mol. Cell. Biol, Vol. 12, pgs.1286–1291 (1992)). An LTR has been isolated from the Myeloproliferative Sarcoma Virus (MPSV). (Chirigos, et al., Int. J. Cancer, Vol. 3, pgs 223–237 (1968)), and has been shown to express more strongly than the Moloney Murine Leukemia Virus LTR in embryonic carcinoma cells (Seliger, et al., Mol. Cell. Biol., Vol. 6, pgs. 286–293 (1986); Hillery, et al., Proc. Nat. Acad. Sci., Vol. 84, pgs. 5232–5236 (1987); Weiher, et al., 1987, Grez, et al., J. Virol., Vol. 65, pgs 4691–4698 (1991)), and in hematopoietic cells. (Ostertag, et al., J. Virol., Vol. 33, pgs. 573–582 (1980)); Stocking, et al., Proc. Nat. Acad. Sci, Vol. 82, pgs. 5746–5750 (1985); Stocking, et al., Virology, Vol. 153 pgs. 145–149 (1986); Bowtell, et al., Mol. Biol. Med., Vol. 4, pgs. 229–250 (1987)). The fundamental difference between the Moloney Murine Leukemia Virus and the Myeloproliferative Sarcoma Virus enhancer repeats is the presence in MPSV of a consensus site for binding the transcription factor Sp1. (Price, et al., J. Virol, Vol. 65, pgs. 1803–1811 (1991)). Sp1 sites have been shown to function regardless of methylation and, thus, may cause the MPSV LTR to be more resistant to transcriptional inactivation than the Moloney Murine Leukemia Virus LTR.

Other negative-acting cis-elements also have been characterized in the Moloney Murine Leukemia Virus sequences. One such element located at the 5' end of the LTR, is a conserved sequence in over 90% of mammalian type C retroviruses and is referred to as the negative control region or ncr. (Flanagan, et al., Virol. Cell. Biol, Vol. 9, pgs. 739–746 (1989)). The ncr sequence has been shown to bind to a nuclear factor, thereby mediating transcriptional repression. (Flanagan, et al., Virol. Cell. Biol., Vol. 12, pgs. 38–44 (1992)).

Another inhibitory element is located at the primer binding site (PBS) of the Moloney Murine Leukemia Virus leader region. (Weiher, et al., 1987; Feuer, et al., J. Virol., Vol. 63, pgs. 2317–2324 (1989), Loh, et al., Mol. Cell. Biol., Vol. 7, pgs. 3775–3784 (1987); Taketo, et al., J. Virol., Vol. 63, pgs. 4431–4433 (1989)). The sequence from the Moloney Murine Leukemia Virus PBS acts by binding a cellular factor which inhibits RNA transcription (Loh, et al., Mol. Cell. Biol., Vol. 10, pgs. 4045–4057 (1990); Petersen, Mol. Cell. Biol., Vol. 11, pgs. 1214–1221 (1991); Kempler, et al., Virology, Vol. 183, pgs. 690–699 (1993)). An endogenous murine retrovirus, d1587rev, was isolated from murine genomic sequences and found to contain a novel PBS sequence which includes adenine at position +160 (Colicelli, et al., J. Virol., Vol. 57, pgs. 37–45 (1987)). Inclusion of the d1587rev PBS in retroviruses allows increased expression in embryonic carcinoma cells as compared with the wild-type Moloney Murine Leukemia Virus PBS. (Akgun, et al., J. Virol., Vol. 65, pgs. 382–388 (1991); Grey, et al., J. Virol., Vol. 65, pgs. 4691–4698 (1991)).

In addition, extensive de novo methylation of cytosine residues in the proviral Moloney Murine Leukemia Virus LTR has been detected in embryonic stem cell lines and in the F9 embryonic carcinoma cell line. (Stewart, et al., Proc. Nat. Acad. Sci., Vol. 79, pgs. 4098–4102 (1982); Niwa, et al, 1983). Although the causal role of methylation in mediating repression of gene expression is still ambiguous, methylation has been associated with the block in transcription of many different genes. (Cedar, Cell, Vol. 53, pgs. 3–4 (1988); Boyes, et al., Cell, Vol. 64, pgs. 1123–1134 (1991)).

Modified retroviral vectors which achieve expression in embryonic cells would have a wide range of applications. Due to their high efficiency of transduction and integration, active retroviral vectors could be very useful tools to transfer genes into embryonic stem cells for the generation of transgenic mice, embryonic stem cell chimeras, and in cell marking studies during embryonic development (Jaenisch, Science, Vol. 240, pgs. 1468–1475 (1988); Cepko, et al., Meth. Enzymol., Vol. 225, pgs. 933–960 (1993)). Also, retroviral expression vectors expressing in embryonic cells also show enhanced expression in hematopoietic stem cells, and thereby provide valuable tools for gene therapy via bone marrow cells.

Efforts have been made to produce retroviral vectors which overcome the inherent inactivity of the Moloney Murine Leukemia Virus transcriptional unit in embryonic cells. One approach has been to produce vectors with an internal promoter to mediate gene transcription in embryonic stem cells, while using the retroviral LTR only for producing a full length viral genome in the packaging cell; (Bowtell, et al., J. Virol., Vol. 62, pgs. 2464–2473 (1988); Guild, et al., J. Virol., Vol. 62, pgs. 3795–3801 (1988); Soriano, et al., J. Virol., Vol. 65, pgs. 2315–2319 (1991)). There is evidence, however, that the Moloney Murine Leukemia Virus enhancer and primer binding site may have negative effects even on heterologous promoters placed internally. (Gorman, et al., Cell, Vol. 42, pgs. 519–526 (1985); Bowtell, et al., (1988)). Another approach involved incorporation of variant elements, which are active in embryonic stem cells, to replace the Moloney Murine Leukemia Virus sequences, such as the enhancer from the Myeloproliferative Sarcoma Virus variant (Hilberg, et al., Proc. Nat. Acad. Sci., Vol. 84, pgs. 5232–5236 (1987)) or from a mutant polyoma virus (Linney, et al., Nature, Vol. 308, pgs. 470–472 (1984)), or the PBS from d1587rev (Weiher, et al., 1987; Grey, et al., 1991). These approaches have had limited success. The reasons for such limited success may be the interaction of multiple inhibitory elements in or near the LTR; thus, single modifications may not be sufficient to overcome completely the barrier to transcriptional activity.

BRIEF DESCRIPTION OF THE DRAWINGS

This invention now will be described with respect to the drawings, wherein:

FIG. 2 is the sequence of the multiple cloning site in the pG1 plasmid;

FIG. 6 is a map of plasmid MP-neo;

FIG. 7 is a map of plasmid MP-ncr-neo;

FIG. 8 is a map of plasmid MP-Thy-neo;

FIG. 10 is a map of plasmid MP-dl-neo;

DETAILED DESCRIPTION OF THE INVENTION

Figure 1:
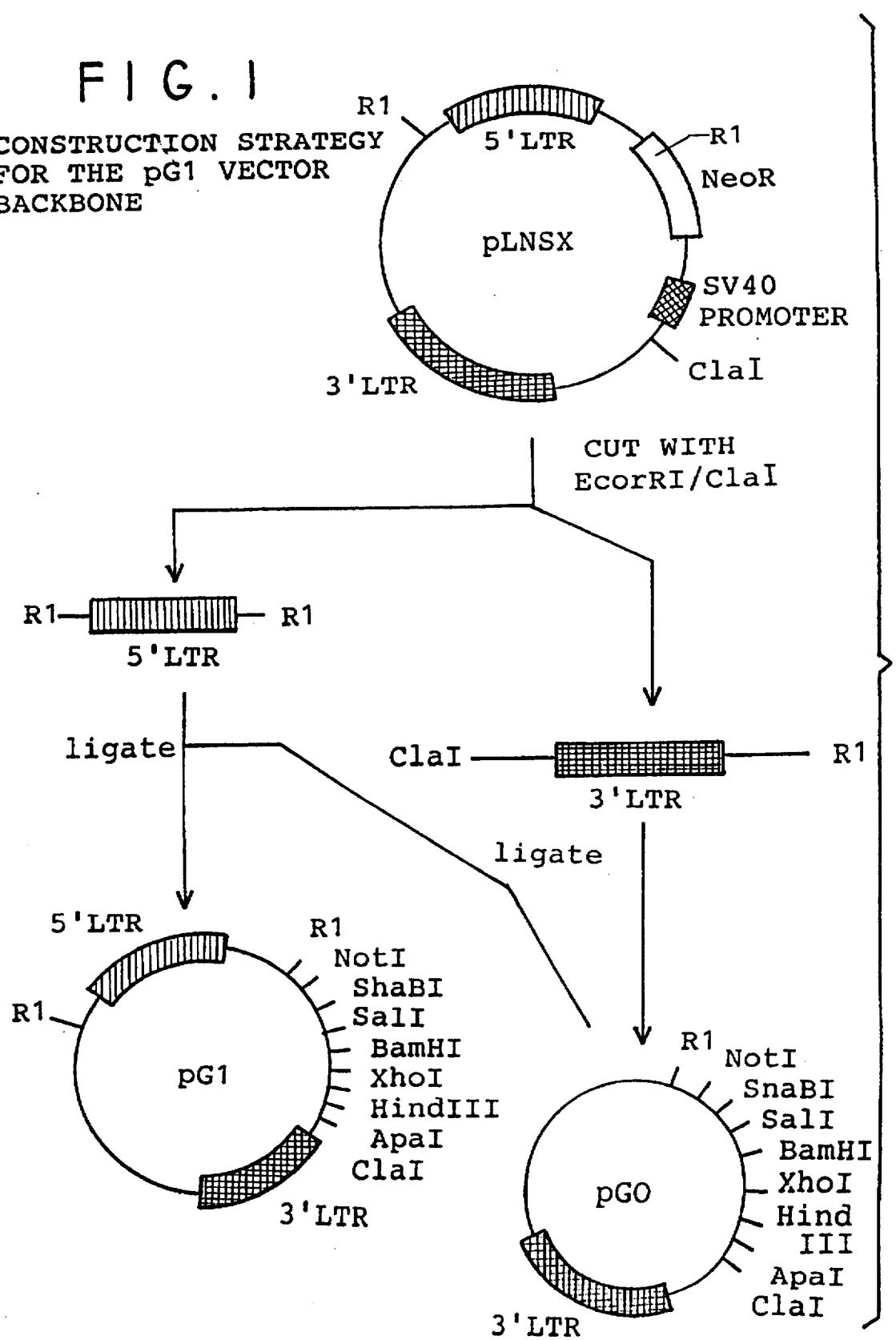
FIG. 1 is a schematic of the construction strategy of the plasmid pG1.

In accordance with an aspect of the present invention, there is provided a retroviral plasmid vector including an enhancer region obtained from a virus selected from the group consisting of Myeloproliferative Sarcoma Virus and polyoma virus, and a primer binding site obtained from murine retrovirus d1587rev. The retroviral plasmid vector does not include a negative control region.

In one embodiment, the enhancer region is obtained from Myeloproliferative Sarcoma Virus. In another embodiment, the enhancer region is obtained from polyoma virus, and in particular from a mutant of polyoma virus. An example of an enhancer region obtained from a mutant of polyoma virus is described further in Valerio, et al., *Gene*, Vol. 84, pgs. 419–427 (1989).

In one embodiment, the retroviral plasmid vector further includes a nucleic acid sequence encoding demethylation. The nucleic acid sequence encoding demethylation in general is a nucleic acid sequence which encodes demethylation of cytosine residues in the proviral LTR. In one embodiment, the nucleic acid sequence encoding demethylation is obtained from the 5' upstream region of the murine Thy-1 gene.

In accordance with another aspect of the present invention, there is provided a retroviral plasmid vector including an enhancer region obtained from a virus selected from the group consisting of Myeloproliferative Sarcoma Virus and polyoma virus; a primer binding site obtained from murine retrovirus d1587rev; and a nucleic acid sequence encoding demethylation. The nucleic acid sequence encoding demethylation may be as hereinabove described.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, Myeloproliferative Sarcoma Virus, and mammary tumor virus. In one embodiment, the retroviral plasmid vector is derived from Moloney Murine Leukemia Virus.

Thus, in accordance with another aspect of the present invention, there is provided a retroviral plasmid vector derived from Moloney Murine Leukemia Virus wherein the enhancer region of the LTR of the Moloney Murine Leukemia Virus has been removed and replaced with an enhancer region from a virus selected from the group consisting of Myeloproliferative Sarcoma Virus and polyoma virus. Also, the primer binding site of the Moloney Murine Leukemia Virus is (a) mutated or (b) removed and replaced with a primer binding site obtained from a retrovirus other than Moloney Murine Leukemia Virus. The negative control region of the Moloney Murine Leukemia Virus also has been deleted.

The primer binding site of Moloney Murine Leukemia Virus is defined as the sequence from base 146 to base 163 of Moloney Murine Leukemia Virus. The term "mutated," as used herein, means that at least one base of the native primer binding site of Moloney Murine Leukemia Virus has been changed to a different base.

In one embodiment, the retroviral plasmid vector further includes a nucleic acid sequence which encodes demethylation. Such nucleic acid sequence may be obtained from the 5' upstream region of the murine Thy-1 gene, as hereinabove described.

In another embodiment, the primer binding site of the Moloney Murine Leukemia Virus is removed and replaced with a primer binding site obtained from a retrovirus other than Moloney Murine Leukemia Virus. In one embodiment, the primer binding site obtained from a virus other than Moloney Murine Leukemia Virus is obtained from murine retrovirus d1587rev.

In accordance with yet another aspect of the present invention, there is provided a retroviral plasmid vector derived from Moloney Murine Leukemia Virus wherein the enhancer region of the LTR of the Moloney Murine Leukemia Virus has been removed and replaced with an enhancer region from a virus selected from the group consisting of Myeloproliferative Sarcoma Virus and polyoma virus, and the primer binding site of the Moloney Murine Leukemia Virus is (a) mutated or (b) removed and replaced with a primer binding site obtained from a retrovirus other than Moloney Murine Leukemia Virus. The vector also includes a nucleic acid sequence encoding demethylation.

In one embodiment, the primer binding site of Moloney Murine Leukemia Virus is removed and replaced with a primer binding site obtained from a retrovirus other than Moloney Murine Leukemia Virus. The primer binding site may be obtained from murine retrovirus d1587rev, as hereinabove described.

In one embodiment, the retroviral plasmid vectors derived from Moloney Murine Leukemia Virus may be derived from the LN series of vectors, as described in Bender, et al., *J. Virol.*, Vol. 61, pgs. 1639–1649 (1987) and Miller, et al., *Biotechniques*, Vol. 7, pgs. 980–990 (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral vector includes each of these cloning sites. Such vectors are further described in U.S. patent application Ser. No. 919, 062, filed Jul. 23, 1992, and incorporated herein by reference in its entirety.

When a retroviral vector including such cloning sites is employed, there may also be provided a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from the shuttle cloning vector to the retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The retroviral plasmid vectors of the present invention may further include at least one nucleic acid sequence encoding a therapeutic agent. The term "therapeutic" is used in a generic sense and includes treating agents, prophylactic agents and replacement agents.

The term "nucleic acid sequence" as used herein, means a DNA or RNA molecule, and more particularly a linear series of deoxyribonucleotides or ribonucleotides connected one to the other by phosphodiester bonds between the 3' and 5' carbons of the adjacent pentoses. Depending on the use herein, such term includes complete and partial gene sequences, and includes polynucleotides as well.

Nucleic acid sequences encoding therapeutic agents include, but are not limited to, nucleic acid sequences encoding tumor necrosis factor (TNF) genes, such as TNF-α; genes encoding inteferons such as Interferon-α, Interferon-β, and Interferon-γ; genes encoding interleukins such as IL-1, IL-1β, and Interleukins 2 through 15; genes encoding G-CSF, M-CSF, and GM-CSF; genes encoding adenosine deaminase, or ADA; the Zap70 kinase gene; genes which encode cellular growth factors, such as lymphokines, which are growth factors for lymphocytes; the glucocerebrosidase gene; genes encoding epidermal growth factor (EGF), and keratinocyte growth factor (KGF); genes encoding soluble CD4; the β-globin gene; Factor VIII; Factor IX; T-cell receptors; the α-iduronidase gene; the LDL receptor, ApoE, ApoC, ApoAI and other genes involved in cholesterol transport and metabolism; the alpha-1 antitrypsin (α1AT) gene; the ornithine transcarbamylase (OTC) gene; the CFTR gene; the insulin gene; suicide genes such as, for example, viral thymidine kinase genes, such as the Herpes Simplex Virus thymidine kinase gene, the cytomegalovirus virus thymidine kinase gene, and the varicella-zoster virus thymidine kinase gene; Fc receptors for antigen-binding domains of antibodies; antisense sequences which inhibit viral replication, such as antisense sequences which inhibit replication of hepatitis B or hepatitis non-A non-B virus; antisense c-myb oligonucleotides; multidrug resistance genes such as the MDR-1 gene; and antioxidants such as, but not limited to, manganese superoxide dismutase (Mn-SOD), catalase, copper-zinc-superoxide dismutase (CuZn-SOD), extracellular superoxide dismutase (EC-SOD), and glutathione reductase; and selectable markers such as the neomycin resistance ($neo^R$) gene, the β-galactosidase (lacZ) gene, the chloramphenicol transferase (CAT) gene, and the NGF-R gene.

The nucleic acid sequence encoding at least one therapeutic agent is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the therapeutic agent. It is to be understood, however, that the scope of the present invention is not to be limited to specific foreign genes or promoters.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, such as hereinabove described, and CaPO$_4$ precipitation. In one alternative, the retroviral plasmid vector may be encapsulated into a liposome, or coupled to a lipid, as hereinabove described, and then administered to a host, also as hereinabove described.

The producer cell line generates infectious retroviral vector particles which include the nucleic acid sequence(s) encoding the therapeutic agent(s). Such retroviral vector particles then may be employed, to transduce eukaryotic cells, either in vitro or in vivo. The transduced eukaryotic cells will express the nucleic acid sequence(s) encoding the therapeutic agent. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

When such retroviral vector particles are employed to transduce eukaryotic cells in vitro, the retroviral vector particles may transduce the eukaryotic cells at a multiplicity of infection (moi) of from about 0.001 to about 10, preferably from about 1 to about 10. The transduced eukaryotic cells then may be administered to a host as part of a gene therapy procedure. Such cells may be administered to a host, which may be mammalian host, a non-human primate host, or a human host, in an amount of from about $1 \times 10^2$ to about $1 \times 10^{11}$ cells, preferably from about $5 \times 10^4$ to about $5 \times 10^8$ cells, more preferably from about $5 \times 10^6$ to about $5 \times 10^8$ cells. The exact dosage of eukaryotic cells is dependent upon a variety of factors, including the age, weight, and sex of the host, the type of cells to be transduced, and the disease or disorder to be treated.

When administered in vivo, the retroviral vector particles are administered to a host in an amount effective to produce a therapeutic effect in a host. In general, the retroviral particles are administered in an amount of from 1 to about 10 particles per cell. The exact dosage of particles to be administered is dependent upon the factors hereinabove described.

The retroviral vectors of the present invention are applicable particularly to the transduction of embryonic cells, and in particular embryonic stem cells. For example, the retroviral vectors could be employed for the transfer of genes into embryonic stem cells for the generation of transgenic animals, embryonic stem cell chimeras, or may be employed in cell marking studies during embryonic development. In addition, retroviral vectors expressing in embryonic cells also may show enhanced expression in hematopoietic stem cells, and therefore such retroviral vectors may be useful for gene therapy via bone marrow cells.

The retroviral vectors of the present invention may be employed in the treatment of a variety of diseases and disorders. Such diseases and disorders include, but are not limited to, genetic disease such as hemoglobinopathies; lysosomal storage diseases; metabolic disorders; immune deficiencies; cancer leukemia; and AIDS.

In addition, the retroviral vector particles may be employed in animal models in order to determine the effectiveness of a gene therapy treatment. In such an animal model, the retroviral vector particles including a gene encoding a therapeutic agent, or eukaryotic cells transduced in vitro with such retroviral vector particles, are administered to an animal. Subsequent to such administration, the animal is tested for expression of the gene encoding the therapeutic agent in the animal. From such testing, one may determine the amount of retroviral particles or eukaryotic cells transduced with such retroviral particles to be administered to a human patient.

Also, the retroviral vector particles may be employed to transduce eukaryotic cells, such as those hereinabove described, in vitro, for the in vitro production of a therapeutic agent, which may be obtained from the culture of transduced eukaryotic cells by methods known to those skilled in the art.

EXAMPLES

The invention now will be described with respect to the following examples; however, the scope of the present invention is not intended to be limited thereby.

EXAMPLE 1

Construction of Vectors

A. Construction of pG1Na.

Figure 3:
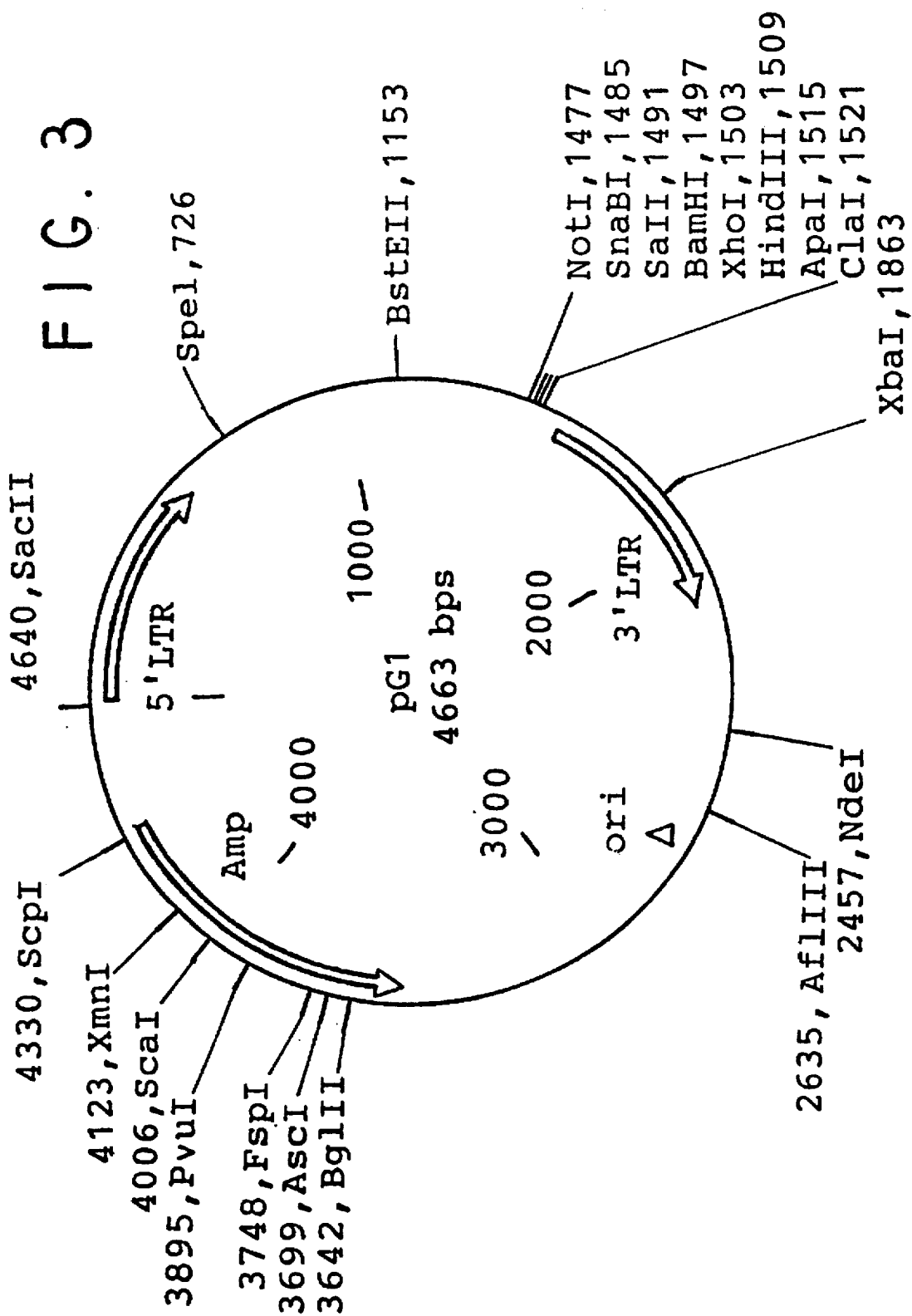
FIG. 3 is a map of plasmid pG1.

Plasmid pG1 was constructed from pLNSX (Palmer, et al., *Blood*, Vol. 73, pgs. 438–445), and incorporated herein by reference. The construction strategy for plasmid pG1 is shown in FIG. 1. The 1.6 kb EcoRI fragment, containing the 5' Moloney Murine Sarcoma Virus (MoMuSV) LTR, and the 3.0 kb EcoRI/ClaI fragment, containing the 3' LTR, the bacterial origin of replication and the ampicillin resistance gene, were isolated separately. A linker containing seven unique cloning sites was then used to close the EcoRI/ClaI fragment on itself, thus generating the plasmid pG0. The plasmid pG0 was used to generate the vector plasmid pG1 (FIG. 3) by the insertion of the 1.6 kB EcoRI fragment containing the 5' LTR into the unique EcoRI site of pG0. Thus, pG1 (FIG. 3) consists of a retroviral vector backbone composed of a 5' portion derived from MoMuSV, a short portion of gag in which the authentic ATG start codon has been mutated to TAG (Bender, et al. 1987), a 54 base pair multiple cloning site (MCS) containing, from 5' to 3' the sites EcoRI, NotI, SnaBI, SalI, BamHI, XhoI, HindIII, ApaI, and ClaI and a 3' portion of MoMuLV from base pairs 7764 to 7813 (numbered as described (Van Beveren, et al., *Cold Spring Harbor*, Vol. 2, pg. 567, 1985), and incorporated herein by reference (FIG. 2). The MCS was designed to generate a maximum number of unique insertion sites, based on a screen of non-cutting restriction enzymes of the pG1 plasmid, the neo$^r$ gene, the β-galactosidase gene, the hygromycin gene, and the SV40 promoter.

Figure 4:
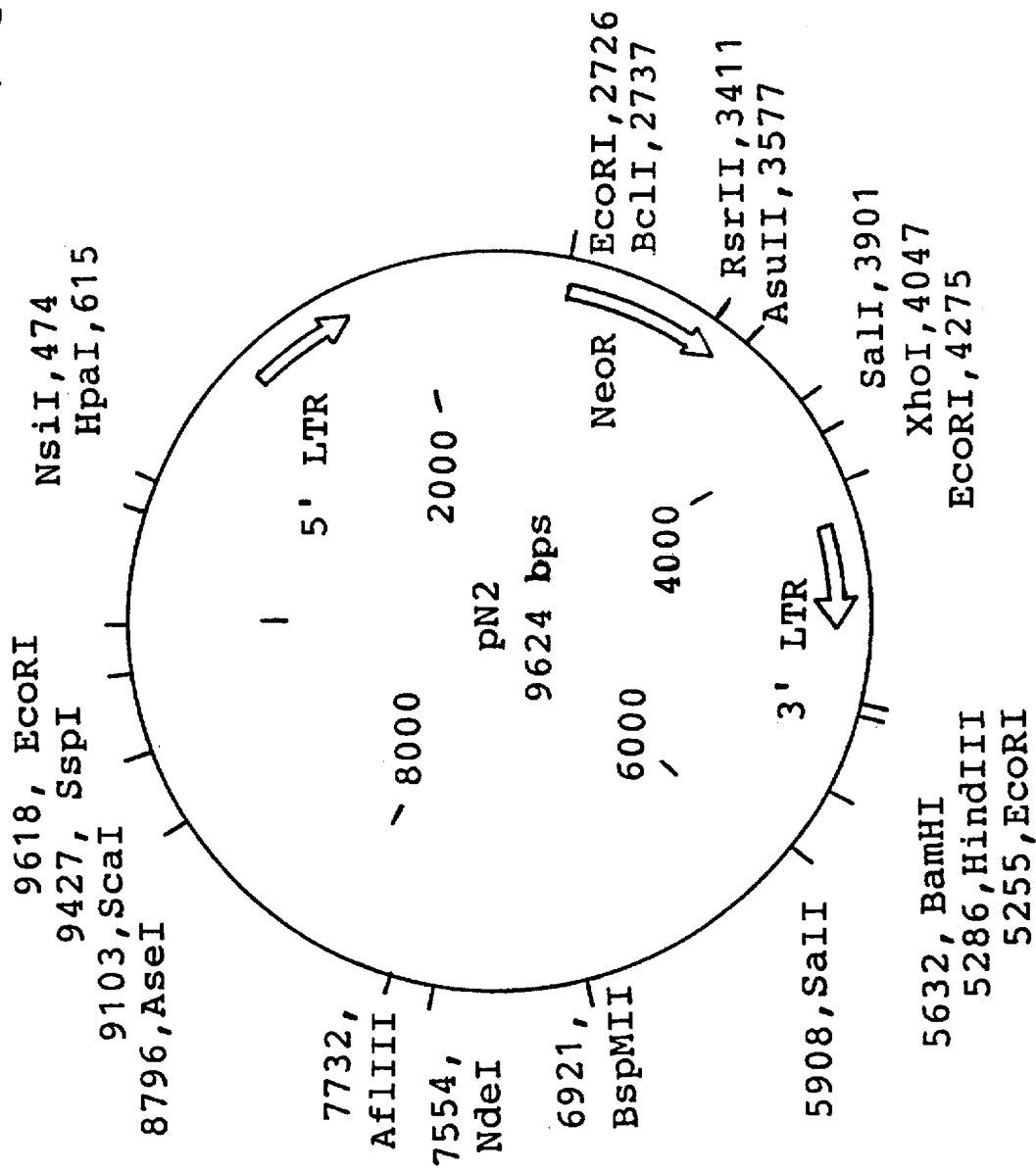
FIG. 4 is a map of plasmid pN2.
Figure 5:
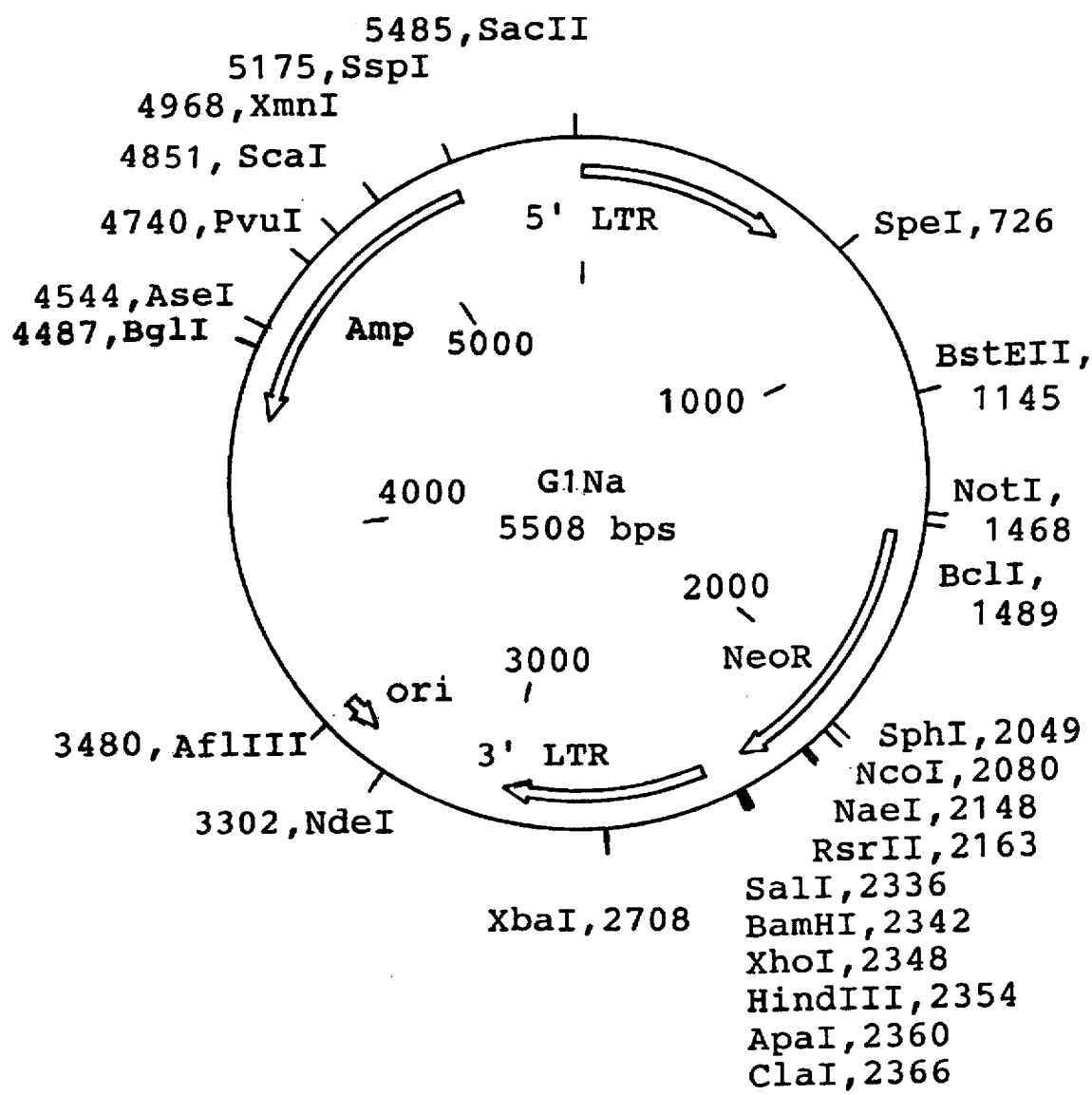
FIG. 5 is a map of plasmid pG1Na.

The "backbone" vector pG1Na was constructed from pG1 and pN2 (Armentano, et al., *J. Virology*, Vol. 61, pgs. 1647–1650 (1987)). pG1Na was constructed by cutting pN2 (FIG. 4) with EcoRI and AsuII, filling in the ends of the EcoRI/AsuII fragment containing the neo$^R$ gene, and ligating the fragment into SnaBI digested pG1 to form pG1Na (FIG. 5).

Figure 9:
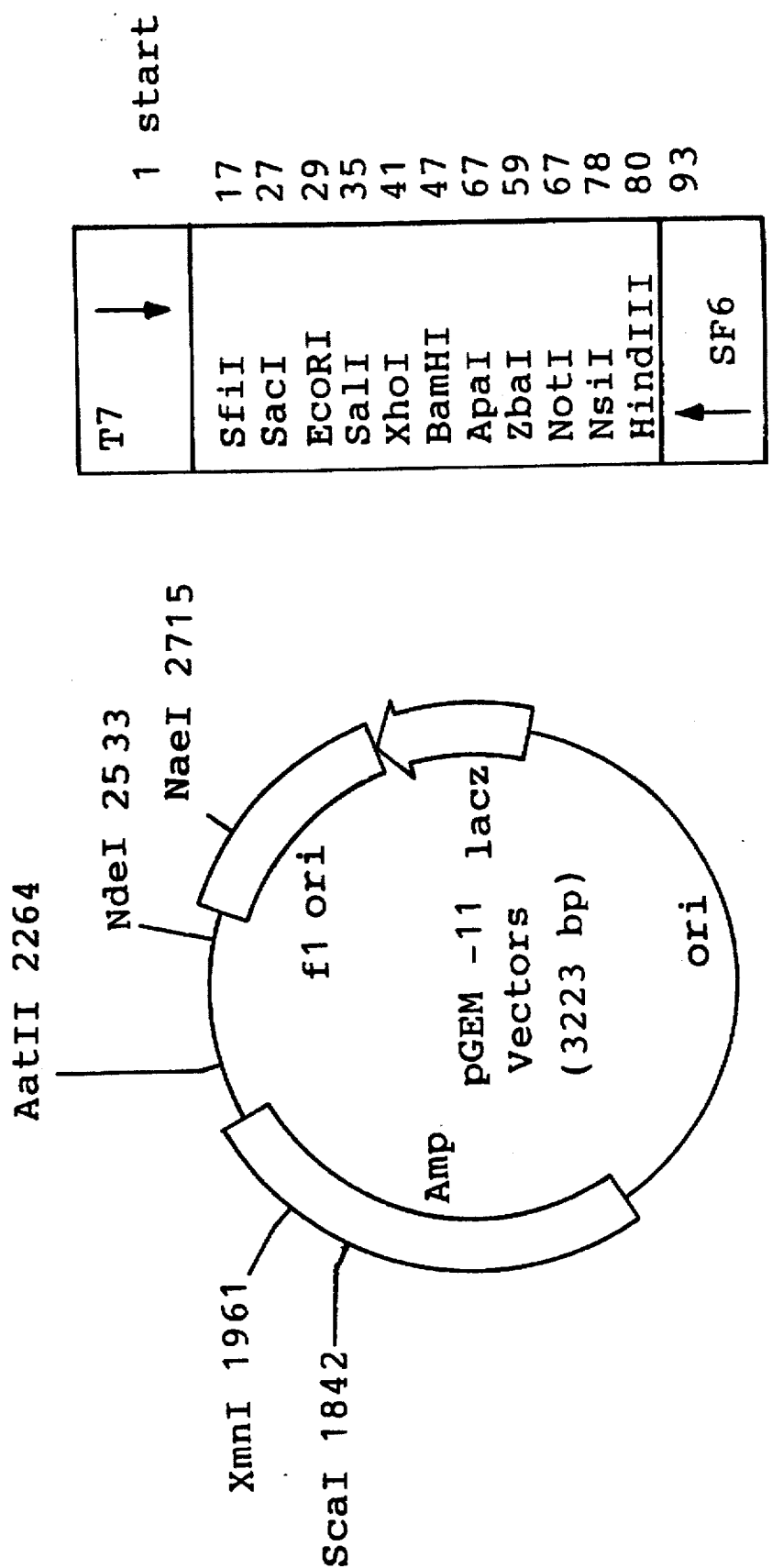
FIG. 9 is a map of plasmid pGEM11.
Figure 11:
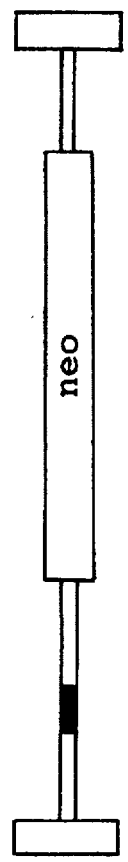
FIG. 11 is a map of plasmid MP-ncr-dl-neo.
Figure 12:
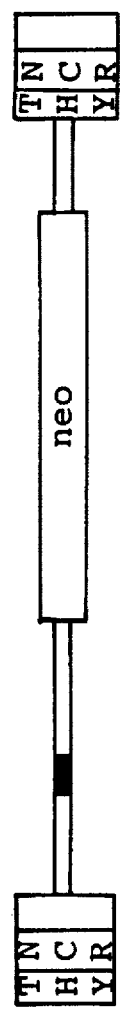
FIG. 12 is a map of plasmid MP-Thy-dl-neo.

B. Construction of MPneo, MPncrneo, MPdlneo, LNncrneo, MPthyneo, MPthydlneo, and MPncrdlneo The Myeloproliferative Sarcoma Virus (MPSV) LTR (provided by W. Ostertag, Heinrich-Pette Institute, Hamburg, Germany) was used to replace the 3' Moloney Murine Leukemia Virus LTR of pG1Na to make MPneo. pG1Na was cut at the ClaI site (bp 2366) and the AccI site (bp 3248) to release the Moloney Murine Leukemia Virus 3' LTR. The 3' LTR from MPSV was cloned into the ClaI-AccI site of pG1Na to make MP-neo. (FIG. 6.) The negative control region (ncr) was removed from the MPSV LTR as an NheI (at nucleotide 33 in the LTR) to Sau3a (at nucleotide 97 in the LTR) fragment. The cut ends of the LTR were ligated together after fill in of the ends by Klenow DNA polymerase to make the MPncr 3'LTR, which then was cloned into the ClaI/AccI site of pG1Na, yielding MPncrneo (FIG. 7). The Thy-1 fragment in the plasmid Bluescript (Stratagene) (provided by M. Szyf, McGill University, Montreal, Canada) was opened at the SmaI site immediately 3' of the insert, and a synthetic XbaI site 5'-CTCTAGAG-3' (New England Biolabs, Beverly, Mass.) was ligated in place. The Thy-1 fragment then was isolated as an XbaI/XbaI fragment and cloned into the NheI site of the MPSV LTR in Bluescript. The Thy-1 substituted MPSV LTR (MPthy) was cloned into the ClaI/AccI site of pG1Na to make MPthyneo (FIG. 8).

pG1Na was cut with EcoRI, which cuts at bp 1460 and bp 5375 to obtain a fragment containing the 5' LTR, the pbs, and the leader (Psi) region. This fragment was subcloned into pGEM11 (Promega). (FIG. 9.) The pbs was removed from this pG1Na-derived fragment as a KpnI/SpeI fragment and replaced with the KpnI/SpeI pbs fragment from d1587 rev. The 5' LTR and leader (Psi) region then was removed from MP-neo with the enzyme EcoRI and replaced with the EcoRI/EcoRI fragment of the 5' LTR-leader region containing the KpnI-SpeI fragment from d1587 rev. This produced the plasmid MP-dl-neo. (FIG. 10.) The same EcoRI/EcoRI fragment with the 5' LTR, d1587 rev pbs, and leader region was substituted into the EcoRI/EcoRI sites of MP-ncr-neo and MP-Thy-neo to make MP-ncr-dl-neo (FIG. 11) and MP-Thy-dl-neo (FIG. 12), respectively.

Figure 14:
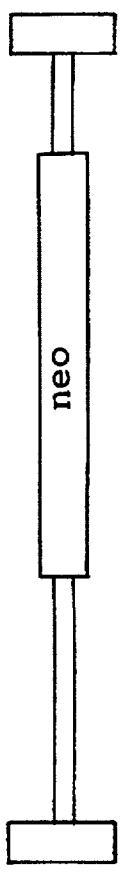
FIG. 14 is a map of LN-ncr-neo.
Figure 13:
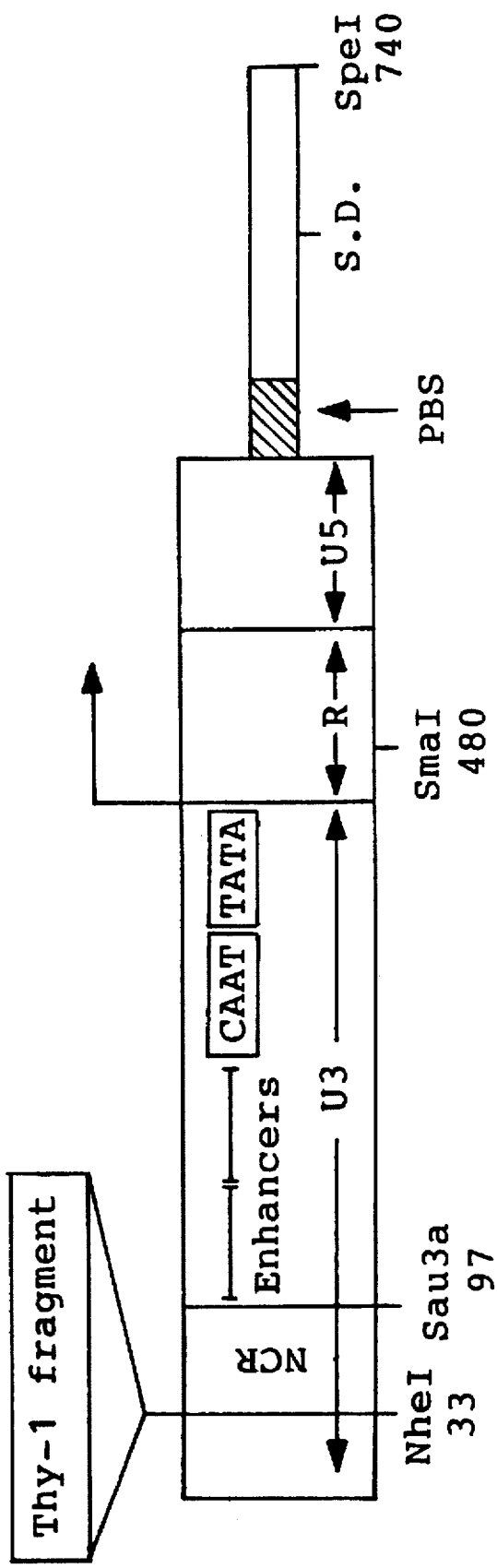
FIG. 13 is a schematic of the modifications introduced in the LTR and leader regions of the retroviral vectors.

To make LNncrneo, the ncr region (NheI at position 33 to Sau3a at position 97; FIG. 13) was deleted from the 3' LTR of pG1Na. Specifically, a portion of the 3'LTR from pG1Na was subcloned into Bluescript as a ClaI/SstI fragment. Then, PCK was performed using primers overlapping the Sau3a site (bp 97), 5'-GACCGCTAGCAGATCTAGGTCAGG-3' (sense) and the SstI site (bp 413), 5'-CTGGAGCTCGGGGAGCAGA-3' (antisense). The sequence of the sense primer included a 5' overhang which contains the recognition site for NheI (boldfaced in primer sequence), followed by sequences overlapping the Sau3a site converting it to a BglII site (underlined in primer sequence). The 320 bp PCR product, which lacks the ncr region, was digested with NheI and SstI and used to replace the 380 bp NheI to SstI fragment of the 3' LTR, effectively removing the ncr and adding a novel BglII site. The ClaI/SbaI fragment containing the ncr deletion in Bluescript was used to replace the ClaI/SbaI portion of the 3' LTR in pG1Na plasmid, producing LNncrneo. (FIG. 14.)

C. Transduction of plasmid vectors into cell lines.

The plasmid vectors MPneo, MPdlneo, MPncrdlneo, LNncrneo, MPthyneo, and MPthydlneo were transfected into the ecotropic packaging cell line GP+E-86 (obtained from A. Bank, Columbia University, New York) using Transfection-Reagent (DOTAP; Boehringer Mannheim Corp., Indianapolis, Ind.) and selection in 0.5 mg/ml of active G418 (Geneticin; GIBCO-BRL, Bethesda, Md.). The GP+E-86 cells were grown under selection pressure in DMEM supplemented with 10% Newborn Calf Serum, hypoxanthine (15 µg/ml), xanthine (250 µg/ml) (Markowitz, et al., *J. Virol.*, Vol. 62, pgs. 1120–1124 (1988)). Culture supernatants were collected and used to transduce the PA317 (ATCC No. CRL 9078) amphotropic packaging cell line. The PA317 cells were grown in DMEM containing 10% FCS. The PA317 cells then were selected in G418 and cell clones were isolated. Supernatants from the clones then were titered by serial dilution on NIH3T3 fibroblasts (ATCC No. 6473) grown in DMEM supplemented with 10% calf serum. High titer clones were derived from the PA317 pools of MPneo, MPdlneo, and MPncrdlneo, whereas high titer pools of MPthyneo, MPthydlneo, and LNncrneo were used in subsequent analyses.

EXAMPLE 2

Viral supernatants in DMEM containing 10% FCS were harvested from confluent 100-mm tissue culture plates of vector producing PA317 fibroblasts and passed through 0.45 µm filters. They were serially diluted ten-fold in a total volume of 5 mls. The dilutions were as follows: undiluted, 1:10, 1:100, 1:1,000, 1:10,000, and no virus. Two milliliters of each dilution were overlayed on each of F9 cells and 3T3 cells plated twenty-four hours earlier at $2.5 \times 10^4$ cells in 6-well tissue culture dishes. Transduction was performed in the presence of 8 µg/ml of polybrene for 2 hrs. Then, the cells were washed in phosphate buffered saline (PBS) and cultured in their respective media. Twenty-four hours later, G418 (GIBCO-BRL) was added at 0.5 mg/ml. Selection was carried out for 12–14 days, until no cells were seen in the non-transduced wells and visible colonies were formed in the transduced wells. Then, the cells were washed in PBS and stained with 0.5% crystal violet in methanol. G418 resistant colonies were counted and the colony forming units per milliliter ($G418^R$ cfu/ml) of viral suspension was calculated. The relative ability of the different vectors to express in F9 cells was quantitated by dividing the effective titer ($G418^R$ cfu/ml) on F9 cells by the titer ($G418^R$ cfu/ml) on 3T3 cells, therefore accounting for differences in the number of infective viral particles among preparations. The results are shown in Table I below.

TABLE I

| | | G418 resistant-CFU per ml of viral preparation | | | | | | |
|---|---|---|---|---|---|---|---|---|
| | Exp# | 1 (Undiluted) | 2 1:10 | 3 1:100 | 4 1:1,000 | 5 1:10,000 | 6 (No virus) | Average |
| LN | F9 | $9.0 \times 10^4$ | $0.75 \times 10^4$ | $0.05 \times 10^4$ | $0.2 \times 10^4$ | $1.3 \times 10^4$ | $0.02 \times 10^4$ | |
| | 3T3 | $50.0 \times 10^5$ | $10.0 \times 10^5$ | $1.6 \times 10^5$ | $8.8 \times 10^5$ | $8.0 \times 10^5$ | $0.85 \times 10^5$ | |
| | F9/3T3 | 0.0180 | 0.0075 | 0.0031 | 0.0023 | 0.023 | 0.023 | 0.0082 |
| MPneo | F9 | $2.9 \times 10^4$ | $0.65 \times 10^4$ | $0.65 \times 10^4$ | $0.2 \times 10^4$ | $3.8 \times 10^4$ | $0.08 \times 10^4$ | |
| | 3T3 | $3.0 \times 10^5$ | $1.8 \times 10^5$ | $1.5 \times 10^5$ | $3.2 \times 10^5$ | $9.5 \times 10^5$ | $0.63 \times 10^5$ | |
| | F9/3T3 | 0.0725 | 0.0361 | 0.0433 | 0.0069 | 0.0400 | 0.0127 | 0.0352 |
| MPdlneo | F9 | $2.5 \times 10^4$ | $1.3 \times 10^4$ | $0.2 \times 10^4$ | $0.4 \times 10^4$ | $1.5 \times 10^4$ | $0.02 \times 10^4$ | |
| | 3T3 | $10.0 \times 10^5$ | $4.0 \times 10^5$ | $1.5 \times 10^5$ | $2.1 \times 10^5$ | $2.9 \times 10^5$ | $0.36 \times 10^5$ | |
| | F9/3T3 | 0.0250 | 0.0325 | 0.0133 | 0.0191 | 0.0517 | 0.056 | 0.0245 |
| LNncrneo | F9 | | | $0.12 \times 10^4$ | $0.2 \times 10^4$ | $1.0 \times 10^4$ | $0.01 \times 10^4$ | |
| | 3T3 | | | $0.75 \times 10^5$ | $2.7 \times 10^5$ | $5.0 \times 10^5$ | $0.31 \times 10^5$ | |
| | F9/3T3 | | | 0.0160 | 0.0078 | 0.0200 | 0.0032 | 0.0118 |
| MPncrdlneo | F9 | $5.7 \times 10^4$ | $10.0 \times 10^4$ | $1.75 \times 10^4$ | $12.0 \times 10^4$ | $69.0 \times 10^4$ | $0.7 \times 10^4$ | |
| | 3T3 | $3.2 \times 10^5$ | $3.5 \times 10^5$ | $2.3 \times 10^5$ | $3.5 \times 10^5$ | $4.0 \times 10^5$ | $0.5 \times 10^5$ | |
| | F9/3T3 | 0.1781 | 0.2857 | 0.0761 | 0.3429 | 1.7250 | 0.1400 | 0.4346 |
| MPthyneo | F9 | $9.9 \times 10^4$ | | $0.12 \times 10^4$ | $0.18 \times 10^4$ | $2.3 \times 10^4$ | $0.02 \times 10^4$ | |
| | 3T3 | $23.0 \times 10^5$ | | $0.65 \times 10^5$ | $1.15 \times 10^5$ | $3.5 \times 10^5$ | $0.18 \times 10^5$ | |
| | F9/3T3 | 0.0391 | | 0.0185 | 0.0157 | 0.0657 | 0.0111 | 0.0300 |
| MPthydlneo | F9 | $1.8 \times 10^4$ | $1.0 \times 10^4$ | $0.4 \times 10^4$ | $1.45 \times 10^4$ | $14.0 \times 10^4$ | $0.32 \times 10^4$ | |
| | 3T3 | $2.0 \times 10^5$ | $2.0 \times 10^5$ | $0.75 \times 10^5$ | $0.9 \times 10^5$ | $3.0 \times 10^5$ | $0.13 \times 10^5$ | |
| | F9/3T3 | 0.090 | 0.050 | 0.0533 | 0.1611 | 0.4667 | 0.2462 | 0.1779 |

As shown in Table I, the standard Moloney Murine Leukemia Virus based vector, LN, showed restricted activity on F9 embryonic carcinoma cells only 1/120 (or 0.0082) as efficiently as compared with NIH 3T3 cells. The presence of the Myeloproliferative Sarcoma Virus enhancer instead of the Moloney Murine Leukemia Virus enhancer resulted in a slight increase in the relative number of G418 resistant cfu/ml formed on F9 cells (0.0352). Substitution of the Moloney Murine Leukemia Virus primer binding site with the dl587rev primer binding site did not increase further the effective titer on F9 cells (0.0245). The vector containing the MPSV enhancer and a deletion of the ncr region in addition to the dl587rev primer binding site (MPncrdlneo), was able to transfer G418 resistance to F9 cells almost half as efficiently as to NIH 3T3 fibroblasts. Presence of the Thy-1 fragment encoding demethylation, in addition to the dl587rev primer binding site resulted in a vector (MPthydlneo) that transferred G418 resistance to F9 cells one-fifth as efficiently as to NIH 3T3 fibroblasts.

EXAMPLE 3

F9 and 3T3 cells were transduced, in parallel, with viral particles generated from the retroviral plasmid vectors hereinabove described, with four rounds exposure to viral supernatant for 3 hours each in 6-well plates. The cells then were cultured for two weeks, and cell pellets were prepared for DNA and RNA extractions.

Genomic DNA and total cellular RNA were extracted from the retrovirally transduced F9 and 3T3 cell pellets for Southern blot and Northern blot analysis. DNA was isolated by SDS/proteinase K and RNase digestion at 55° C. for 3 to 4 hours. The digested samples were extracted with phenol-chloroform, the DNA was precipitated in ethanol, and resuspended in TE buffer. (Sambrook, et al., *Molecular Cloning: A Laboratory Manual*, 2nd edition, Cold Spring Harbor Laboratory Press, (1989)). A quantitative Southern blot was performed to measure proviral copy number. Control and sample DNA (10 µg) were digested with the restriction enzyme SstI(GIBCO-BRL) which cuts once in each LTR, thereby releasing the full length proviral sequence. To obtain a standard curve, DNA from a PA317 clone containing a single copy of the neo gene was diluted with DNA from the parental PA317 cells. The dilutions were 100%, 50%, 10%, 5%, and 0%. The digested DNA's were electrophoresed on a 1.3% agarose gel, denatured, and blotted onto a nylon membrane. The filter then was probed with $^{32}$P-labeled neo DNA (Feinberg, et al., *Anal. Biochem.*, Vol. 137, pg. 266 (1984)) and used to expose Kodak X-OMAT films (Eastman-Kodak, Rochester, N.Y.) at −70° C. After satisfactory exposures were obtained, the membrane was stripped and rehybridized with a 1.6 kb human glucocerebrosidase cDNA probe to permit quantitation of differences in DNA loading. The filter was analyzed again by autoradiography. Densitometric analysis was performed on the Southern blot (FIG. 15) using the U.S. Biochemical Sci. Scan 5000 (Cleveland, Ohio).

Figure 15A:
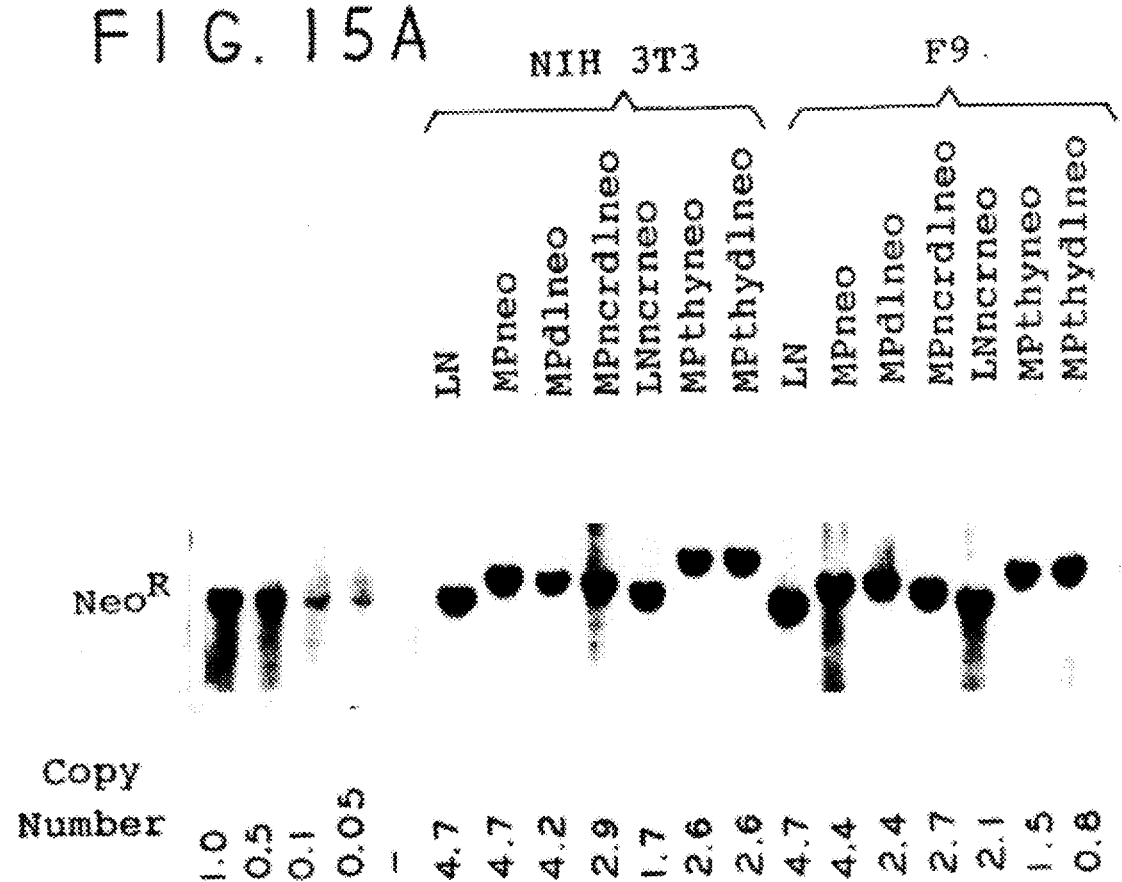
FIGS. 15A and 15B are a quantitative Southern blot analysis of gene transfer efficiency by the retroviral vectors into NIH T3 cells and F9 cells.
Figure 15B:
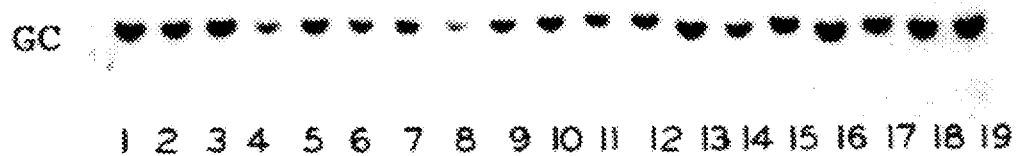

The Southern blot included a standard curve for copy number made by serially diluting genomic DNA extracted from a PA317 cell line containing one copy per cell of the LN provirus (FIG. 15; lanes 1–5). A copy number standard curve was plotted by measuring the intensity of the provirus neo signal by densitometry and normalizing the results to the glucocerbrosidase endogenous marker thereby accounting for differences in loading between DNA samples. The provirus copy number in the transduced NIH 3T3 cells (FIG. 15; lanes 6–12) and F9 cells (FIG. 15; lanes 13–19) was derived from the standard curve. Similar transduction efficiencies were achieved by the different vectors in the F9 cells and in the NIH 3T3 cells, with limited experimental variations.

For the Northern blot, RNA was isolated by the acid guanidinium thiocyanate—phenolchloroform method described in Chomczynski, et al., *Anal. Biochem.*, Vol. 163, pgs. 156–159 (1987). 15 µg of RNA were electrophoresed on a 1.2% formaldehyde gel, denatured, neutralized, and transferred to a nylon membrane by capillary blotting. The filter was hybridized with $^{32}$P-labeled neo DNA and used to expose x-ray films at −70° C. The filter was analyzed using the Betascope 603 Blot Analyzer (Betagen, Waltham, Mass.) to quantitate the level of RNA. The filter then was stripped, rehybridized with a mouse β-actin DNA probe, and analyzed again by autoradiography. The Northern blot is shown in FIG. 16.

Figure 16A:
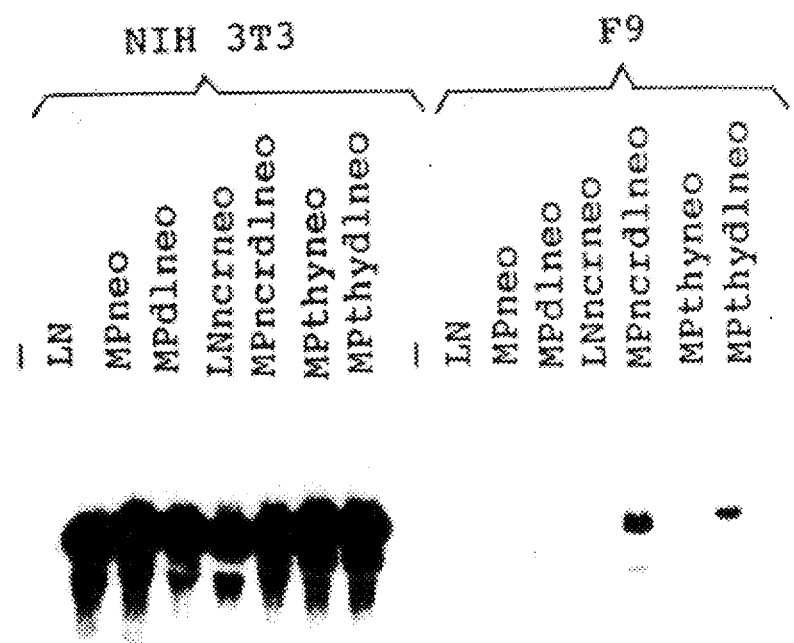
FIGS. 16A and 16B are a Northern blot analysis of stably transduced NIH 3T3 and F9 cells.
Figure 16B:
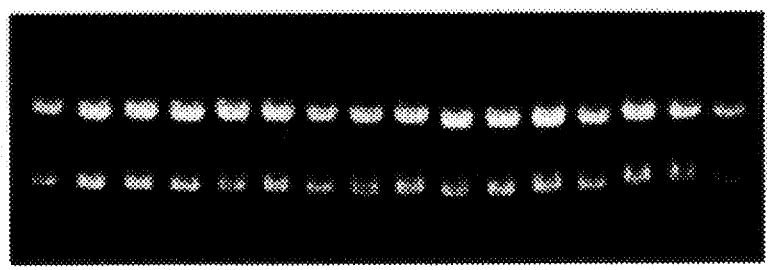

All seven vectors expressed at similar levels in the NIH 3T3 fibroblasts (FIG. 16; lanes 1–8). No RNA transcription, however, was detected in the F9 cells from the LN, MPneo, MPdlneo, LNncrneo, and MPthyneo vectors. (FIG. 16; lanes 10–13 and 15). The two vectors containing three modifications, MPncrdlneo and MPthydlneo, promoted detectable levels of RNA transcription in F9 cells (FIG. 16; lanes 14 and 16.).

EXAMPLE 4

Methylation Analysis

Figure 17A:
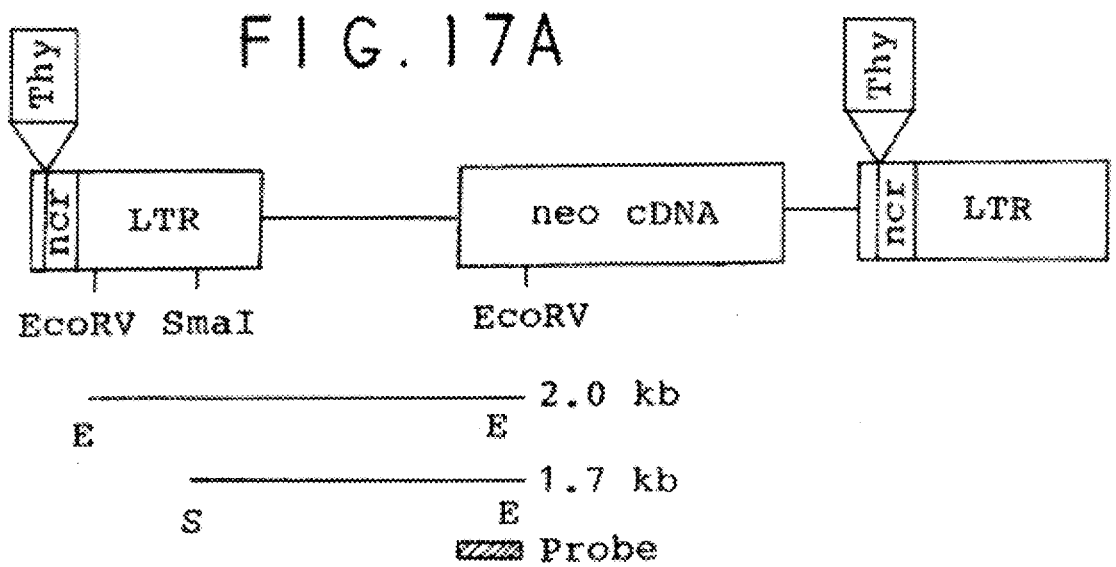
FIG. 17A is a schematic of the modified retroviral vectors showing the location of restriction enzyme sites and of the probe used for methylation analysis of the retroviral vectors in F9 cells by Southern blot.
Figure 17B:
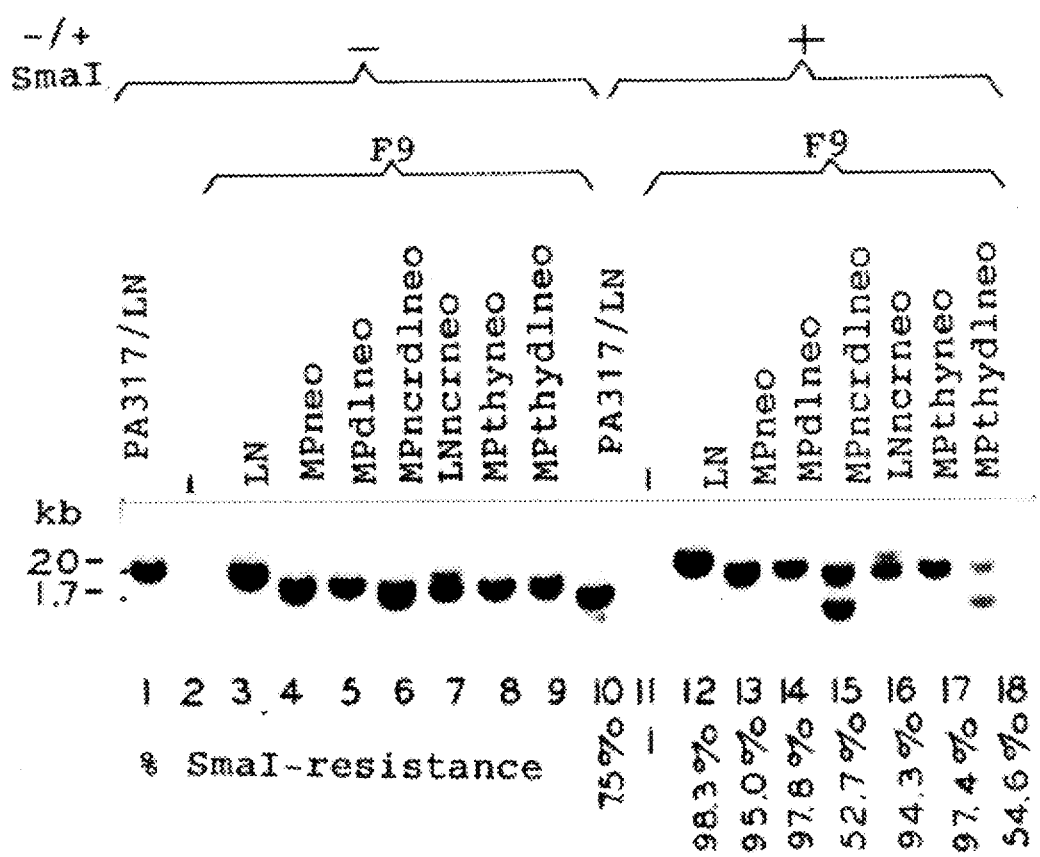
FIG. 17B is a Southern blot of genomic DNA from stably transduced F9 cells which was digested with BamHI and either EcoRV alone, or EcoRV and SmaI.

Genomic DNA (15 µg), from F9 cells transduced with the retroviral vectors hereinabove described, was digested with the restriction enzyme BamHI (New England Biolabs, Beverly, Md.) to reduce the size of the high molecular weight DNA, followed by digestion with EcoRV (GIBCO-BRL). Then, half of each DNA sample was digested with the methylation-sensitive restriction enzyme SmaI (New England Biolabs). In order to monitor completeness of the enzyme digestions, a 20 µl sample of the digestion mixture was mixed with lambda DNA (GIBCO-BRL) for EcoRV digestion and Adenovirus Type 2 DNA (GIBCO-BRL) for SmaI digestion. The mixtures were incubated in parallel with the main samples at 37° C. and run subsequently on an agarose check gel. EcoRV and EcoRV/SmaI digested genomic DNA were electrophoresed on a 1.5% agarose gel, denatured, and blotted to a nylon membrane. The blots were hybridized with a 285 bp probe from the 5' end of the neogene at the Not I site to the PvuII site in the pG1Na plasmid. Several exposures of the blot were obtained on X-ray films. The autoradiograms were analyzed on a U.S. Biochemical Sci. Scan 5000 measuring the relative intensities of the SmaI-sensitive and SmaI-resistant bands. A schematic of the modified retroviral vectors showing the location of the EcoRV and SmaI restriction enzyme sites, and the probe used for methylation analysis, as well as 2.0 kb and 1.7 kb bands generated after SmaI digestion, are shown in FIG. 17A. The blot is shown in FIG. 17B. Lanes 1–9 are blots of genomic DNA from stably transduced F9 cells which were digested with BamHI and EcoRV alone, and lanes 10–18 are blots of genomic DNA from stably transduced F9 cells which were digested with BamHI, EcoRV, and SmaI. This figure also depicts the values of percentage SmaI resistance of the proviruses as the relative intensities of the 2.0 kb and 1.7 kb bands generated after SmaI digestion. The values represent the average obtained from analyzing two different exposures of the same blot.

The SmaI site is methylated heavily in the Moloney Murine Leukemia Virus LTR of the LN vector in F9 cells, showing an SmaI resistance of 98.3% (FIG. 17B; lane 12).

The vectors MPneo, MPdlneo, LNncrneo, and MPthyneo did not show any significant decrease in methylation, with recorded values of SmaI resistance of 95.0%, 97.8%, 94.3%, and 97.4%, respectively. (FIG. 17B; lanes 13, 14, 16, and 17). The vectors MPncrdlneo and MPthydlneo were significantly less methylated than the parent vectors, with 52.7% and 54.6% SmaI resistance, respectively (FIG. 17B; lanes 15 and 18). The simultaneous incorporation of three modifications in the Moloney Murine Leukemia Virus based vector decreases the state of methylation of the provirus in F9 embryonic carcinoma cells, in parallel to the increase in RNA transcription.

EXAMPLE 5

Sequencing of 5'LTR

In the above examples the 5'LTR and leader regions of the proviruses were sequenced, first in the PA317 cells, then in the F9 cells, to ensure correct duplication and maintenance of all the modifications after packaging and serial transduction.

The proviral sequences were amplified by PCR of genomic DNA using primers to the 5' end of the LTR (5'-GACCCCACCTGTACGTATGGCAA-3', sense) and 5' end of the neogene (5'-GCTGGCCAGGTTAACTCCC-3', antisense). The 1.7–1.9 kb PCR products were purified by electrophoresis on a 1.2% agarose gel and extracted using the Qiaex Gel Extraction Kit (Qiagen Inc., Chatsworth, Calif.). Then, sequencing was performed using the Circum-Vent Thermal Cycle Sequencing Kit (New England Biolabs) by internal labeling with $^{35}$S-dATP and cycle sequencing. For sequencing the enhancer region, the primer at the 5' end of the LTR (described above) was used; for the PBS region, oligonucleotides from the splice donor site (5'-GCTGGCCAGGTTAACTCCC-3', antisense) and the R/U5 region (5'-TGCATCCGAATCGTGGTCTC-3', sense) were used. A primer from the Thy-1 sequence (5'-TCGGGGTGGAGCAGTCTTCT-3', sense) allowed sequencing of the enhancer region of the two vectors containing the Thy-1 fragment.

EXAMPLE 6

Vectors MP-neo; MP-ncr-neo; MP-Thy-neo; MP-dl-neo; MP-ncr-dl-neo; and MP-Thy-dl-neo were transduced into primary murine embryonic stem cells of the CCE line (Bradley, et al., *Nature*, Vol. 309, pgs. 255–256 (1984)). The transduced cells were expanded in culture for two weeks without G418 selection, and harvested for nucleic acid analysis. The results are similar to those seen in the F9 cells. The 5' LTR of the vectors showed complete methylation, except for those of MP-ncr-dl-neo and MP-Thy-dl-neo. These two vectors showed that approximately 50% of the LTR could be cut with SmaI, thus demonstrating that there is significantly decreased methylation in these vectors. Northern blot analysis showed that these two vectors also yielded detectable levels of vector-derived transcripts; all others did not produce detectable levels of RNA. Thus, these vectors are active transcriptionally in primary embryonic stem cells. Introduction of exogenous genes into embryonic stem cells using these vectors may be used to generate transgenic mice expressing the inserted gene, such as, for example, an interleukin, including Interleukins 1 through 15; a transcriptional factor; a homeobox gene; or a surface antigen gene.

The activity of these novel vectors has important relevance to human gene therapy. A key technical requisite for effective gene therapy is persistent expression of the inserted gene in the patient's cells. Studies in mice and rats have shown that genes inserted into primary cells, including bone marrow stem cells, hepatocytes, and muscle cells, may be "silenced" after return of the cells into the living animal. It has been demonstrated that in the murine gene transfer/bone marrow transplantation model the Moloney Murine Leukemia Virus LTR of the vector becomes silenced in association with methylation of the cytosines of the LTR. Thus, vectors which resist methylation and remain active may be employed effectively in gene therapy.

The disclosure of all patents, publications (including published patent applications), and database entries referenced in this specification are specifically incorporated herein by reference in their entirety to the same extent as if each such individual patent, publication, and database entry were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. A Maloney Murine Leukemia Virus vector comprising
   (i) a Maloney Murine Leukemia Virus LTR including an enhancer region wherein the enhancer region of the LTR has been removed and replaced with an enhancer region obtained from Myeloproliferative Sarcoma Virus; and wherein
   (ii) the Moloney Murine Leukemia Virus primer binding site is removed and replaced with a primer binding site obtained from murine retrovirus d1587rev, and wherein the Moloney Murine Leukemia Virus negative control region has been deleted.

2. A Moloney Murine Leukemia Virus vector comprising
   (i) a Moloney Murine Leukemia Virus LTR including an enhancer region wherein the enhancer region of the LTR has been removed and replaced with an enhancer region obtained from Myeloprolieferative Sarcoma Virus; and wherein
   (ii) the Moloney Murine leukemia Virus primer binding site is removed and replaced with a primer binding site obtained from murine retrovirus d1587rev; and wherein
   (iii) said vector includes a nucleic acid sequence which decreases methylation of said vector.

3. The vector of claim 4 wherein said vector further comprises at least one nucleic acid sequence encoding a protein.

4. The vector of claim 2 wherein said vector further comprises at least one nucleic acid sequence encoding a protein.

5. An isolated infectious retrovirus particle containing the vector of claim 3.

6. Isolated eukaryotic cells transduced with the retrovital particles of claim 5.

7. The cells of claim 6 wherein said cells are embryonic carcinoma cells.

8. Isolated packaging cells transduced with the vector of claim 4.

9. An isolated infectious retrovital particle containing the vector of claim 4.

10. Isolated eukaryotic cells transduced with the retrovital vector pallcities of claim 9.

11. The cells of claim 10 wherein said cells are embryonic carcinoma cells.

12. Isolated packaging cells transduced with the vector of claim 3.

* * * * *